US012650067B2

(12) United States Patent (10) Patent No.: US 12,650,067 B2
Gunaratne et al. (45) Date of Patent: Jun. 9, 2026

(54) SYSTEMS AND METHODS FOR ANALYTIC MAPPING OF THE METAGEOMIC AND HYDROCARBON FOOTPRINTS OF GEOLOGIC SUBZONES

(71) Applicants:Chevron U.S.A. Inc., San Ramon, CA (US); University of Houston System, Houston, TX (US)

(72) Inventors: Preethi Gunaratne, Houston, TX (US); Gemunu Gunaratne, Houston, TX (US); Gautam Phanse, Sugar Land, TX (US); Courtney A. Kohl, Houston, TX (US); Ulises Salazar, Pascagoula, MS (US); Micah Castillo, Houston, TX (US); Parthasarathy Bhagavatula, Houston, TX (US); Caroline Studnicky, Midland, TX (US); Brandi Elaine Denton Johnson, Spring, TX (US); Timothy John Tokar, The Woodlands, TX (US)

(73) Assignees: Chevron U.S.A. Inc., San Ramon, CA (US); University of Houston System, Houston, TX (US)

( * ) Notice: Subject to any disclaimer, the term of this patent is extended or adjusted under 35 U.S.C. 154(b) by 358 days.

(21) Appl. No.: 18/269,429

(22) PCT Filed: Aug. 31, 2021

(86) PCT No.: PCT/US2021/048339
§ 371 (c)(1),
(2) Date: Jun. 23, 2023

(87) PCT Pub. No.: WO2022/139889
PCT Pub. Date: Jun. 30, 2022

(65) Prior Publication Data
US 2024/0060410 A1 Feb. 22, 2024

Related U.S. Application Data

(60) Provisional application No. 63/129,948, filed on Dec. 23, 2020.

(51) Int. Cl.
| | |
|---|---|
| *E21B 43/30* | (2006.01) |
| *C12Q 1/6888* | (2018.01) |
| | (Continued) |

(52) U.S. Cl.
CPC ......... *E21B 43/305* (2013.01); *G01N 33/243* (2024.05); *G16B 99/00* (2019.02); *C12Q 1/6888* (2013.01); *E21B 49/00* (2013.01)

(58) Field of Classification Search
CPC ..... E21B 49/00; E21B 43/305; C12Q 1/6888; G01N 33/243; G16B 99/00
See application file for complete search history.

(56) References Cited

U.S. PATENT DOCUMENTS

| | | | | |
|---|---|---|---|---|
| 2014/0288853 A1* | 9/2014 | Dreyfus | ................. | G01N 29/14 |
| | | | | 702/27 |
| 2015/0247941 A1* | 9/2015 | Fiduk | ..................... | E21B 49/00 |
| | | | | 702/11 |
| 2017/0370213 A1* | 12/2017 | Knight | ................... | E21B 47/11 |

FOREIGN PATENT DOCUMENTS

| | | | | |
|---|---|---|---|---|
| CN | 104220697 A | * 12/2014 | ............ | E21B 47/02 |

OTHER PUBLICATIONS

Smith MB et al.,2015. Natural Bacterial Communities Serve as Quantitative Geochemical Biosensors. mBio 6:10.1128/mbio.00326-15. (Year: 2015).*
(Continued)

*Primary Examiner* — Catherine T. Rastovski
*Assistant Examiner* — Nyla Gavia
(74) *Attorney, Agent, or Firm* — Esplin & Associates, PC

(57) ABSTRACT
The present disclosure relates to analytic mapping of meta-genomic and hydrocarbon footprints of geologic subzones.
(Continued)

A plurality of DNA profiles are generated based on a set of distinct geological specimens from each well of a plurality of wells. BioGeo markers, BioGeo signatures and a BioGeo matrix are generated based on the plurality of DNA profiles.

20 Claims, 7 Drawing Sheets

(51) Int. Cl.
| | |
|---|---|
| *E21B 49/00* | (2006.01) |
| *G01N 33/24* | (2006.01) |
| *G16B 99/00* | (2019.01) |

(56) References Cited

OTHER PUBLICATIONS

PCT International Search Report and Written Opinion, International Application No. PCT/US2021/048339, mailed Dec. 1, 2021 (7 pages).

* cited by examiner

FORMATION X

FORMATION Y

HORIZONTAL #4

HORIZONTAL #2

HORIZONTAL #3

HORIZONTAL #1

TRANSITION ACROSS LAYERS

SYSTEMS AND METHODS FOR ANALYTIC MAPPING OF THE METAGEOMIC AND HYDROCARBON FOOTPRINTS OF GEOLOGIC SUBZONES

CROSS-REFERENCE TO RELATED APPLICATION

The present application is a national stage application of International Application No. PCT/US2021/048339, filed Aug. 31, 2021, which claims the benefit of U.S. Provisional Application No. 63/129,948, entitled "SYSTEMS AND METHODS FOR ANALYTIC MAPPING OF THE METAGEOMIC AND HYDROCARBON FOOTPRINTS OF GEOLOGIC SUBZONES," which was filed on Dec. 23, 2020, the entirety of which is hereby incorporated herein by reference.

TECHNICAL FIELD

The present disclosure relates to drilling, fracking, reservoir management and understanding the behavior of these systems. More particularly, the present disclosure relates to systems and methods for computing parameters used for exploration, appraisal, and development of hydrocarbon reservoirs, like fracture/drainage heights, percent contribution, well connectivity, oil potential etc. and the changes of such parameters over time by mapping the metagenomic and hydrocarbon footprints of geologic sub-zones ('metageome').

SUMMARY

The present disclosure relates to analytic mapping of metagenomic and hydrocarbon footprints of geologic sub-zones. A plurality of DNA profiles may be generated based on a set of distinct geological specimens from each well of a plurality of wells. BioGeo markers, BioGeo signatures, and a BioGeo matrix may be generated based on the plurality of DNA profiles.

In some implementations, fracture/drainage height from each of the wells of the plurality of wells may be determined based on the plurality of DNA profiles.

In some implementations, a percent contribution from each of the wells of the plurality of wells may be determined based on the plurality of DNA profiles.

In some implementations, a percent contribution from fractures in each stage of the wells of the plurality of wells may be determined based on the plurality of DNA profiles.

In some implementations, stage contribution along a horizontal well of the plurality of wells may be determined based on the plurality of DNA profiles.

In some implementations, well connectivity for each of the wells of the plurality of wells may be determined.

In some implementations, the distinct geological specimens may include at least one of cuttings, drilling mud, and produced fluids.

In some implementations, a map of the hydrocarbon footprint may be generated based on the plurality of DNA profiles. The map of the hydrocarbon footprint may be displayed on a graphical user interface.

In some implementations, fracture lengths of the plurality of wells may be determined based on the plurality of DNA profiles.

In some implementations, generating the plurality of DNA profiles may include, for each DNA profile of the plurality of DNA profiles: extracting genomic signatures specifying each geological specimen, and discriminating each geological specimen from other geological specimens. Changes in specific combinations of DNA species may be determined both spatially and temporally based on the DNA profiles.

Further details and aspects of exemplary embodiments of the present disclosure are described in more detail below with reference to the appended figures.

BRIEF DESCRIPTION OF THE DRAWINGS

A better understanding of the features and advantages of the disclosed systems and methods, and other inventive features, will be obtained by reference to the Detailed Description that sets forth illustrative embodiments, in which the principles of the disclosed systems and methods are described, and the accompanying figures of which.

DETAILED DESCRIPTION

Figure 1:
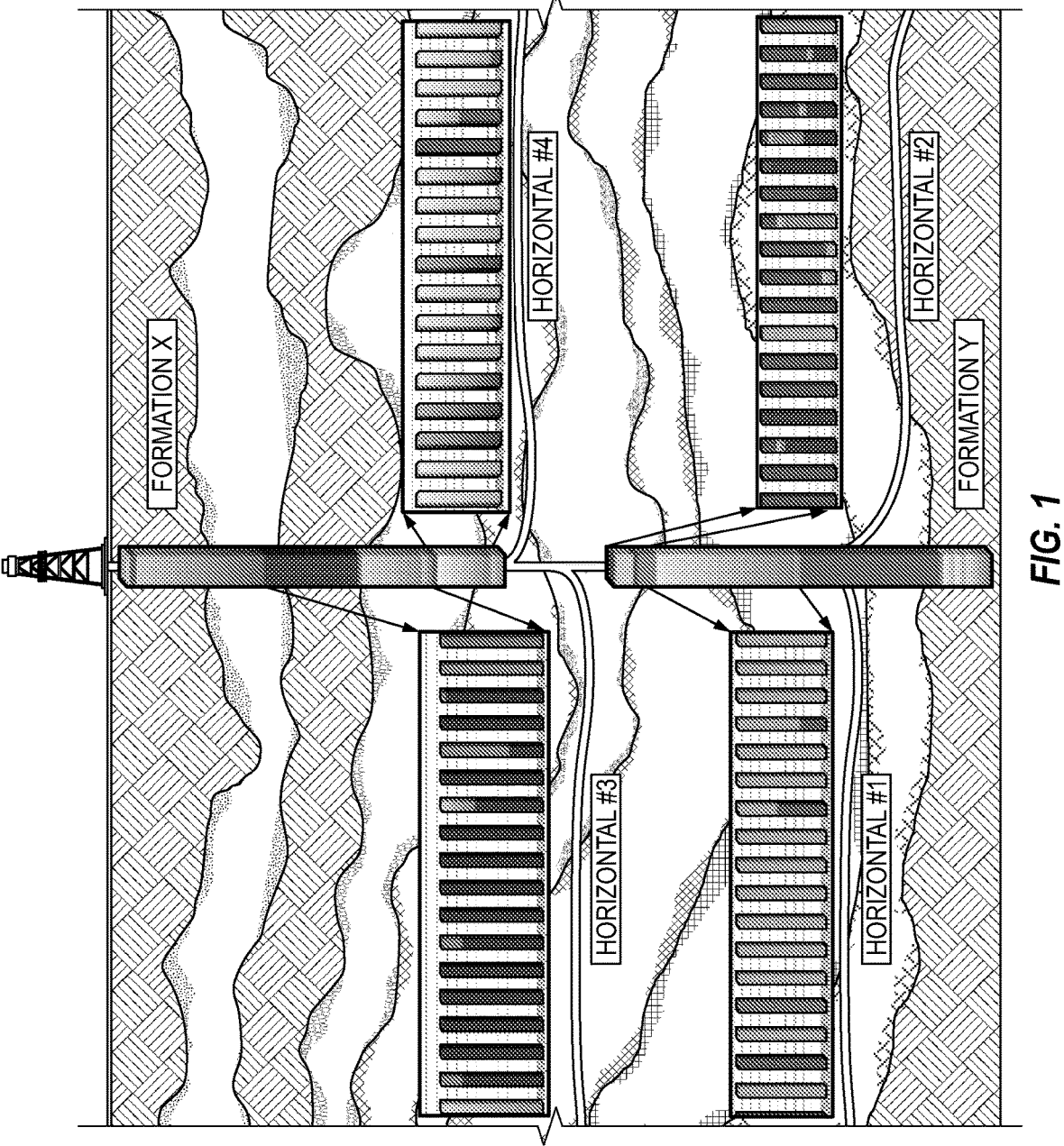
FIG. 1 is a diagram of different geological formations showing variability in species and abundance across both the vertical and horizontal depths.

The present disclosure relates to directional drilling in industrial practice. More particularly, the present disclosure relates to a system and method for mapping the metagenomic and hydrocarbon footprints of geologic sub-zones to compute parameters like fracture/drainage heights, percent contribution, well connectivity, and oil potential to enable optimum design of exploration of oil from reservoir.

Although the present disclosure will be described in terms of specific embodiments, it will be readily apparent to those skilled in this art that various modifications, rearrangements, and substitutions may be made without departing from the spirit of the present disclosure.

For purposes of promoting an understanding of the principles of the present disclosure, reference will now be made to exemplary embodiments illustrated in the figures, and specific language will be used to describe the same. It will nevertheless be understood that no limitation of the scope of the present disclosure is thereby intended. Any alterations and further modifications of the inventive features illustrated and described herein, and any additional applications of the principles of the present disclosure as illustrated and described herein, which would occur to one skilled in the relevant art and having possession of this disclosure, are to be considered within the scope of the present disclosure.

Directional and horizontal drilling has been instrumental in reducing the footprint of gas field development by enabling the production from multiple wells from a single pad location and thereby increasing the length and breadth of the "pay zone." Hydraulic fracturing designed to extract oil from impermeable zones and tap into previously inaccessible resources has had some success but in some cases the recovery rates are <10% of the oil trapped. This is largely because microseismic surveys, petrophysical logs, geochemistry data, and chemical tracers designed for conventional and offshore oil exploration have not performed well in relation to the exploration of 'oil trapped' in low permeability zones. It is contemplated that natural gas exploration is within the scope of the present disclosure but oil is described for exemplary purposes.

The multivariate, heterogeneous nature of oil and natural gas reservoirs is one barrier to the application of conventional methods to accurately predict dynamic shifts in the flow of oil in shale rock over the period of the production cycle. An innovative and inventive predictive analytic system or predictive analytic platform is described in this disclosure that exploits the multivariate, heterogeneous nature of reservoirs to map the metageome (genetic material found in subsurface soil, metagenome of subsurface material) to extract a high-resolution map of reservoir dynamics. The predictive analytic system integrates next generation sequencing and a multi-modular big data analysis pipeline to delineate the metageome and hydrocarbon footprints of geologic subzones, including shale rock.

The metageome of a given reservoir includes the DNA footprint of the comprehensive set of biological species including present-day fauna and flora and fossilized genomic fragments (that once thrived and survived) in each geological subsurface zone in geological time. DNA is extracted from subsurface microbes that live in fracture networks and the pore spaces of rocks, by sampling cuttings (rock shavings) and mud obtained from drilling. The extracted DNA is subjected to whole genome sequencing (WGS) and/or selected panel amplicon sequencing (SPAS).

The term "BioGeo markers" as used herein includes a biomarker of a geological profile. BioGeo markers are based on the similarities and differences of DNA from biological fauna and flora and biological fossils extracted from defined subsurface zones (i.e., approximately every 5-1000 feet on the vertical hole and every 5-1000 feet on each of the horizontal wells).

Figure 6:
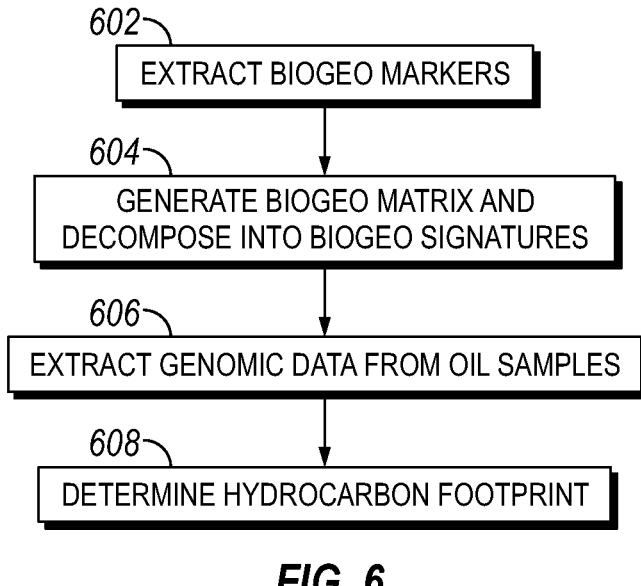
FIG. 6 describes the process of mapping of the reservoir hydrocarbon footprint in geological zones of interest using metageome data.

FIG. 6 describes the process of mapping of the reservoir hydrocarbon footprint in geological zones of interest using metageome data.

At step 602, sequence file from samples is processed through the predictive analytic system to extract BioGeo markers based on the similarities and differences of DNA from biological fauna and flora and biological fossils extracted from defined subsurface zones.

At step 604, the BioGeo markers that represent significant variability observed in the original matrix are integrated to generate BioGeo Matrix. The BioGeo Matrix represents the metagenomic footprint of the basin of interest. The BioGeo Matrix is now further decomposed to give the BioGeo Signatures (BioGeo Sigs) for each of the zones.

At step 606, genomic data is extracted from oil samples from the wellhead collected at regular intervals. The data is subjected to whole genome sequencing (WGS) and selected panel amplicon sequencing (SPAS) and mapped on the BioGeo matrix.

At step 608, hydrocarbon footprint for a given basin is determined by applying time series methodologies to extract the causal relationships among the dominant BioGeo Sigs enriched in production fluids. The dynamics of ecological communities are influenced by interspecific competition and cooperation for survival in a specific set of environmental conditions at multiple temporal and spatial scales. The information in the unobserved variables is encoded in the observed time series, and a single time series can, therefore, be used to reconstruct the original state space.

The disclosed technology can improve the accuracy of prediction in dynamic shifts in the flow of oil in shale rock over the period of the production cycle and provide novel insights into the distribution of hydrocarbon potential and reservoir dynamics to support a plan for maximum production through the controlled commingling of zones from multiple optimally spaced laterals. The sheer reduction in the number of well pads based on 'smart' well spacing strategies afforded by the technology of the present disclosure is expected to not only result in significant economic gains through the increase in hydrocarbon production, and improvements in reserves recovery in heterogeneous or multilayered reservoirs for the asset owners, but also substantial environmental benefits that are congruent with the current environmental standards and regulations.

Hydraulic fracturing designed to extract oil and/or natural gas from impermeable zones and tap into previously inaccessible resources has had some success but in some cases the recovery rates are <10% of the oil trapped. This is largely because 1) microseismic surveys, petrophysical logs, geochemistry data, and chemical tracers designed for conventional and offshore oil exploration have not performed well in relation to the exploration of oil trapped in low permeability zones; and 2) accurate prediction of dynamic shifts in the flow of oil in shale rock over the period of the production cycle is hindered by the multivariate and heterogeneous nature of these reservoirs.

DNA sequences representing the microbiome (the sum total of microbial organisms extracted from natural subsurface samples) can be used to monitor reservoir characteristics across time to provide a dynamic view of the changes during the production cycle. However, the microbiome represents only one of the components of the metagenome (microbial organisms+eukaryotic species) of reservoirs and therefore is inadequate by itself to capture some of the critical changes in reservoir characteristics before and after drilling and production processes.

The predictive analytic platform and system disclosed herein significantly increases the number of variables over the current state-of-the-art by capturing and sequencing all extractable DNA signals by using a combination of multiplexed selected panel amplification and whole-genome sequencing that captures microbial and eukaryotic species.

The predictive analytic platform of this disclosure can provide a high-resolution view of the dynamic changes in reservoir characteristics, before and after drilling and production processes, using an integrated set of network modules described below.

The predictive analytic platform of this disclosure utilizes all DNA signals from the comprehensive set of biological species including present-day fauna and flora and fossilized genomic fragments (that once thrived and survived) in each geological subsurface zone in geological time to delineate the DNA footprint of the entire reservoir and utilizes the information to predict the hydrocarbon footprint in each geological subsurface zone.

The platform and system of this disclosure integrates multiple network modules of big data analysis tools and adapts the application to create a high-resolution biomarker map of reservoirs to address critical problems in the oil and natural gas industries including fracture heights from DNA signatures extracted from produced fluids; percent contribution of each of the fracture heights to production from a given horizontal well; differentiating between well connectivity and signature sharing; and predicting yet to be tapped areas with oil potential in a given reservoir.

BioGeo signatures may be extracted that describe the metagenomic landscape (BioGeo matrix) of oil fields, reservoirs, and geological zones of interest to predict landing zones, fracture heights, and percent contribution of oil and natural gas. This information may be used for planning future wells, including locations, completion plans, and fracturing. DNA fingerprints of geological samples (i.e., cuttings and mud from vertical and horizontal drilling) may be extracted based on the similarities and differences between present-day biological fauna and flora and biological fossils, which may be used to generate BioGeo markers for each geological subsurface zone. The term "BioGeo Signatures" (BioGeo Sigs) includes a BioGeo marker context matrix (BioGeo Matrix) which is created for each pad using a non-negative matrix factorization (NNMF) algorithm, and the matrix is decomposed to compute the total number of BioGeo markers that can explain 90% of the variability observed in the original matrix. NNMF is a matrix factorization method where matrices are constrained to be non-negative. Produced fluids collected at specific intervals (i.e., bi-weekly collections) are processed through the next-generation sequencing and big data analytics platform described above to extract BioGeo Sigs in accordance with this disclosure. The BioGeo Sigs for the vertical drill hole are then compared with BioGeo Sigs from each of the horizontal pads and produced fluids from each horizontal well in further accordance with this disclosure.

Analysis may be performed using a framework that performs genomic identification of significant targets on the frequent signatures across the entire cohort to identify peaks of signal amplification and deletion. A correlation matrix is established and used as the primary input for a highly parallelized BioGeo Sig Set Enrichment Analysis (BGSEA), and leading-edge BioGeo Sigs are visualized using circular visualization plots to estimate the fracture heights and percent contributions from each of the fractures.

A geological specimen includes a sample from a well drilled from a drill hole. The goal of the analysis is to compare and contrast DNA profiles from distinct geological specimens extracted from defined intervals in space (e.g., cuttings from every 5-1000 feet of a vertical hole and every 5-1000 feet from one of more lateral wells drilled from that specific vertical drill hole) and/or time (e.g., production fluids from fracking operations every monitored two weeks). An algorithm is presented that extracts common genomic signatures specifying each specimen and, most importantly, discriminating each specimen from all other specimens tested to predict from the DNA profiles changes in the specific combinations of DNA species both spatially and temporally. The challenge is the inherent "low signal to noise" in such datasets, i.e., the most robustly abundant DNA species play no useful role in the analysis because of the lack of spatial and temporal variability. Furthermore, they mask the 'useful signals' from the less abundant species. The analytical approach in accordance with this disclosure is designed to (1) identify and eliminate this irrelevant data, and (2) partition or "cluster" the specimens. The outline of the approach is described below.

The method includes performing genomic identification of significant targets analysis of the frequent BioGeo Sigs across the entire cohort to identify peaks of amplification and deletion. The method further includes performing unsupervised hierarchical clustering using the contribution of each signature over the samples and divide the BioGeome of the reservoir into a distinct number of clusters (BioGeo clusters). The unsupervised hierarchical clustering may be performed by a neural network or other suitable machine learning network.

The method further may include identifying the optimal subgroup of DNA species that can optimally differentiate between samples. Toward this end, a measure referred to as non-dimensionalized standard deviation is used.

The expression is $$\sigma = \frac{\sqrt{\mathrm{Var}(X)}}{E\{\,|\,X - E[X]\}},$$

where E[X] denotes the expectation of a random variable X. A sequential max-min algorithm may also be used for this purpose. For the implementation, each gene is characterized using its levels in the available specimens. Thus the DNA species is expressed as the expression levels of the DNA species in the specimen. The next step is to find out how the characterization can be reduced, i.e., to find a small set of DNA species that can be used for the purpose.

Once a pre-specified number of DNA species are selected, the abundance levels of that set is used for clustering.

A second approach to find a reduced DNA species set defining a certain geologic subregion is persistent homology. The reduced DNA species sets are used to address issues of signature sharing. The optimal reduced subgroup of DNA species from the sample is searched and matched against the BioGeo Matrix.

The use of subsurface biomarkers (e.g., subsurface DNA) includes several benefits. Microbes that live in the fracture networks and pore space of rocks both reflect and define the subsurface. The use of subsurface biomarkers allows for capturing stratigraphy and lateral heterogeneity at a higher resolution than current methods applied to the subsurface. Subsurface DNA can be used to guide well spacing, determine oil potential, evaluate well communication, evaluate the need for repeating hydraulic fracturing or other workover in a well, and understand production profiling. Subsurface DNA is a non-invasive, high-resolution data source that enables integrated analysis across production life cycles and does not require downhole tool deployment or added environmental risk. Because microbes are sensitive to environmental conditions, their DNA signatures will reflect changing reservoir conditions, such as fracturing, early flow back, and production.

The use of subsurface biomarkers allows for mapping the hydrocarbon footprint of oil fields, reservoirs, and geological zones of interest. For example, unsupervised hierarchical clustering of the genomic identification of significant targets analysis is performed using the contribution of each signature over the samples to divide the BioGeome of the reservoir into a distinct number of clusters (BioGeo clusters).

Various statistical methods like ANOVA, Welch's t-test, Chi Square test, K Means and others are used to cluster BioGeo Sigs across the entire basin and decomposed to determine the optimal number of clusters that partition the basin into discrete BioGeo Clusters using Silhouette analysis.

The dominant BioGeo Sigs computed from production fluids should reflect the DNA footprint of hydrocarbon potential (hydrocarbon footprint), based on the dynamics of ecological communities being influenced by the competing interests of all living species occurring at multiple temporal and spatial scales.

The hydrocarbon footprint of a given basin is constructed by extracting the the causal relationships among the dominant BioGeo Sigs enriched in production fluids using time series statistical tests like Granger casualty, Dickey-Fuller test, Convergent Cross-Mapping, Durbin-Watson Statistic or other such methods.

Applying the disclosed technology herein to multi-variable dynamical systems, such as oil wells, can be used to predict oil potential from locations that are yet to be tapped through horizontal well pads or hydraulic fracturing.

A method to map the hydrocarbon footprint of oil fields, reservoirs, and geological zones of interest includes predicting fracture heights, estimating a percent contribution from each of the wells, predict commingling and well connectivity, and detecting counterfeiting and of oil through hydrocarbon signature matching.

The data analytics pipeline consists of establishing the context matrix for an area of interest, Validating the matrix accuracy, predicting fracture heights and percent contribution for individual visits, and predicting overall fracture heights and percent contribution from each of the wells. Establishing the context matrix for an area of interest includes generating sequence data, constructing signatures of the dominant biological fauna, extracting the minimum number of signatures representing variability observed in the entire sample set, and decomposing the signatures to create a context matrix for the entire area of interest. Validating the matrix accuracy includes carrying out unsupervised clustering of sequence data, and predicting landing zones based on a biomarker of biological fauna present and absent. Predicting fracture heights and percent contributions for the individual visit includes carrying out unsupervised clustering of sequence data from samples, mapping on the context matrix to resolve "shared signatures," and predicting fracture heights from individual visits. Predicting overall fracture heights and percent contribution includes carrying out unsupervised clustering of sequence data from production fluids (PFs) from all visits against selected VC, and decomposing all visits into one and map on the context matrix to resolve 'shared signatures and predict fracture heights from each lateral.

Figure 7:
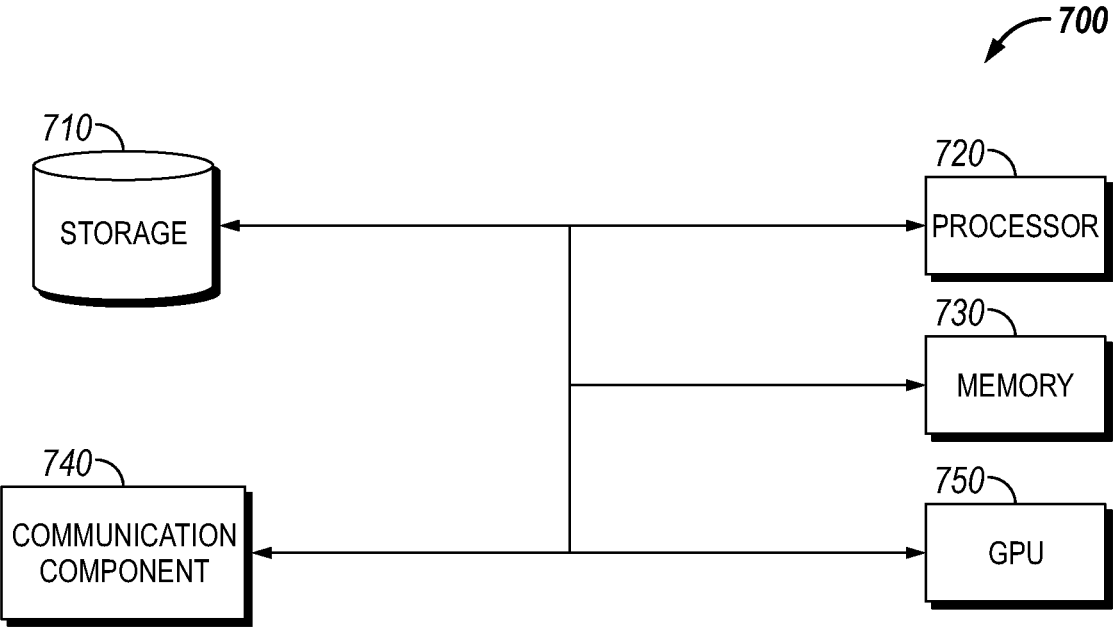
FIG. 7 is a block diagram of a controller, in accordance with this disclosure.

Referring now to FIG. 7, high-level block diagram of an exemplary computing system 700 that may be used with the present disclosure. The computing system 700 may include a processor or controller 720 that may be or include, for example, one or more central processing unit processor(s) (CPU), one or more Graphics Processing Unit(s) (GPU or GPGPU), a chip or any suitable computing or computational device, an operating system, a memory 730, a storage 710, input devices and output devices. A communication component 740 of the computing system 700 may allow communications with remote or external devices, e.g., via the Internet or another network, via radio, or via a suitable network protocol such as File Transfer Protocol (FTP), etc.

The neural networks of the disclosed method may be trained on the computing system or on a remote computing system (e.g., a remote server).

A database can be located in the storage 710. The term "storage" may refer to any device or material from which information may be capable of being accessed, reproduced, and/or held in an electromagnetic or optical form for access by a computer processor. A storage may be, for example, volatile memory such as RAM, non-volatile memory, which permanently hold digital data until purposely erased, such as flash memory, magnetic devices such as hard disk drives, and optical media such as a CD, DVD, Blu-ray disc, or the like.

In machine learning, a Deep Learning Neural network (DNN) may include a convolutional neural network (CNN), which is a class of artificial neural network (ANN), most commonly applied to analyzing data. The convolutional aspect of a CNN relates to applying matrix processing operations to localized portions of the data, and the results of those operations (which can involve dozens of different parallel and serial calculations) are sets of many features that are used to train neural networks. A CNN typically includes convolution layers, activation function layers, and pooling (typically max pooling) layers to reduce dimensionality without losing too many features. Additional information may be included in the operations that generate these features. Providing unique information that yields features that give the neural networks information can be used to ultimately provide an aggregate way to differentiate between different data input to the neural networks.

Figure 8:
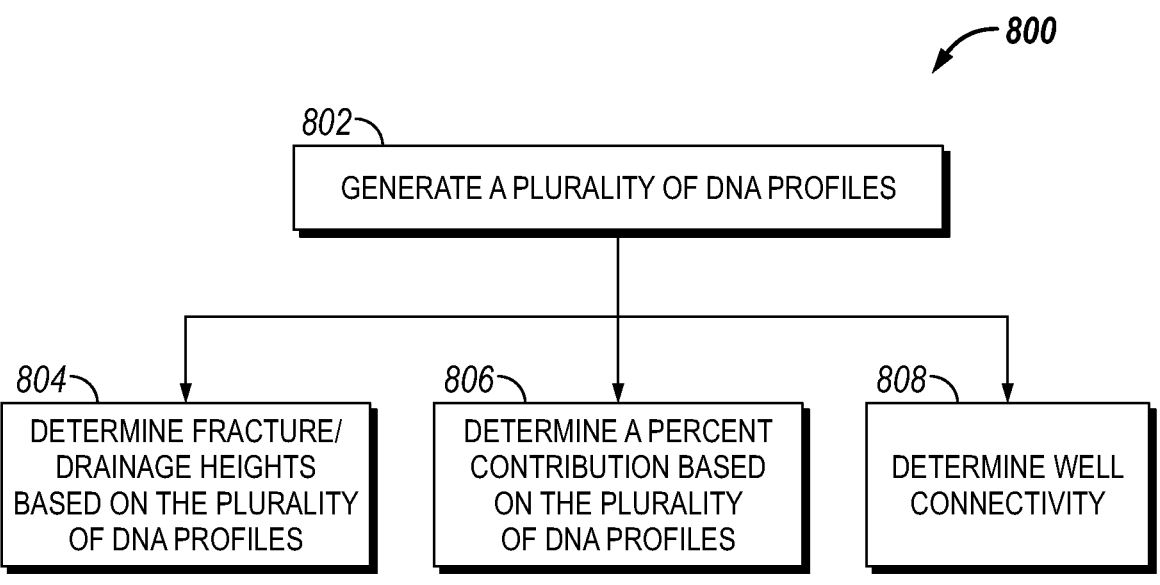
FIG. 8 is a flow diagram of a method for mapping the metagenomic and hydrocarbon footprints of geologic sub-zones to compute fracture/drainage heights, percent contribution of the fracture heights, and well connectivity, in accordance with this disclosure.

The flow diagram of FIG. 8 shows a computer implemented method 800 for mapping the metagenomic and hydrocarbon footprints of geologic sub-zones. Persons skilled in the art will appreciate that one or more operations of the method 800 may be performed in a different order, repeated, and/or omitted without departing from the scope of the disclosure. Two or more operations of the method 800 may be performed in parallel or in sequence. In some methods in accordance with this disclosure, some or all operations in the illustrated method 800 can be operated on the controller 700 (see FIG. 7). Other variations are contemplated to be within the scope of the disclosure. The operations of FIG. 8 will be described with respect to a computing device, or any other suitable computing system device or location thereof including a remotely disposed computing device. It will be understood that the illustrated operations are applicable to other systems and components thereof as well.

At step 802 the controller generates a plurality of DNA profiles based on distinct geological specimens from each well of a plurality of wells. The wells may be drilled in a subsurface region. A DNA profile of a well may refer to a representation of geological specimens from the well. A DNA profile of a well may refer to a representation of DNA of geological specimens from the well. One or more DNA profiles may be generated for a well. For example, one DNA profile may be generated for entirety of a well. As another example, separate DNA profiles may be generated for separate parts of a well. Distinct geological specimens from a well may refer to geological specimens specific to the well. Distinct geological specimens from a well may refer to geological specimen that are extracted from the well, such as from cuttings, drilling mud, produced fluids, and/or other materials extracted from the well. Geological specimens may refer to specimens found under the surface of the Earth. Geological specimens may refer to specimens that were buried within subsurface layers. Geological specimens may include specimens that are current alive on Earth and/or specimens that are extinct. For example, a DNA profile may include a representation of DNA of bacteria, fungus, or other organisms/remains of organisms found in cuttings, drilling mud, produced fluids, and/or other materials extracted from the well.

A DNA profile may provide representation of geological specimens for different segments of the well. A DNA profile may provide representation of geological specimens that are recovered from different segments of the well. A DNA profile may provide representation of geological specimens at different locations in a subsurface region from which the geological specimens were recovered. A DNA profile may provide representation of geological specimens by including information that represents, defines, characterizes, or identifies the identity of geological specimens at different locations, amount/concentration of geological specimens at different locations, ratios of geological specimens at different locations, and/or other information relating to geological specimens at different locations. A DNA profile may provide a fingerprint what type and/or amount of geological specimens exist at different locations in a subsurface region. A DNA profile provide may provide information on changes (e.g., appearance, disappearance, increase, decrease) in geological specimens at different locations.

A DNA profile of a well may be generated by extracting genomic signatures specifying each geological specimen in the well (each geological specimen extracted from a sample from the well), and discriminating each geological specimen in the well from other geological specimens. Discriminating geological specimens may include identifying a representation of the geological specimen that is unique to a location in the subsurface region.

FIG. 1 is a diagram of different geological formations showing variability in species and abundance across both the vertical and horizontal depths. Different shading of bars in FIG. 1 may represent different concentration/frequencies of different species found from samples (e.g., cuttings) in different locations. Abundance of different species are shown for two vertical parts and four horizontal parts of the well. As can be seen in FIG. 1, a species that is located along the vertical part(s) of the well do not necessary exist (e.g., at all, in same frequency) as you move away from the vertical. The variability of species in different locations vary greatly across both vertical and lateral depths.

Figure 2:
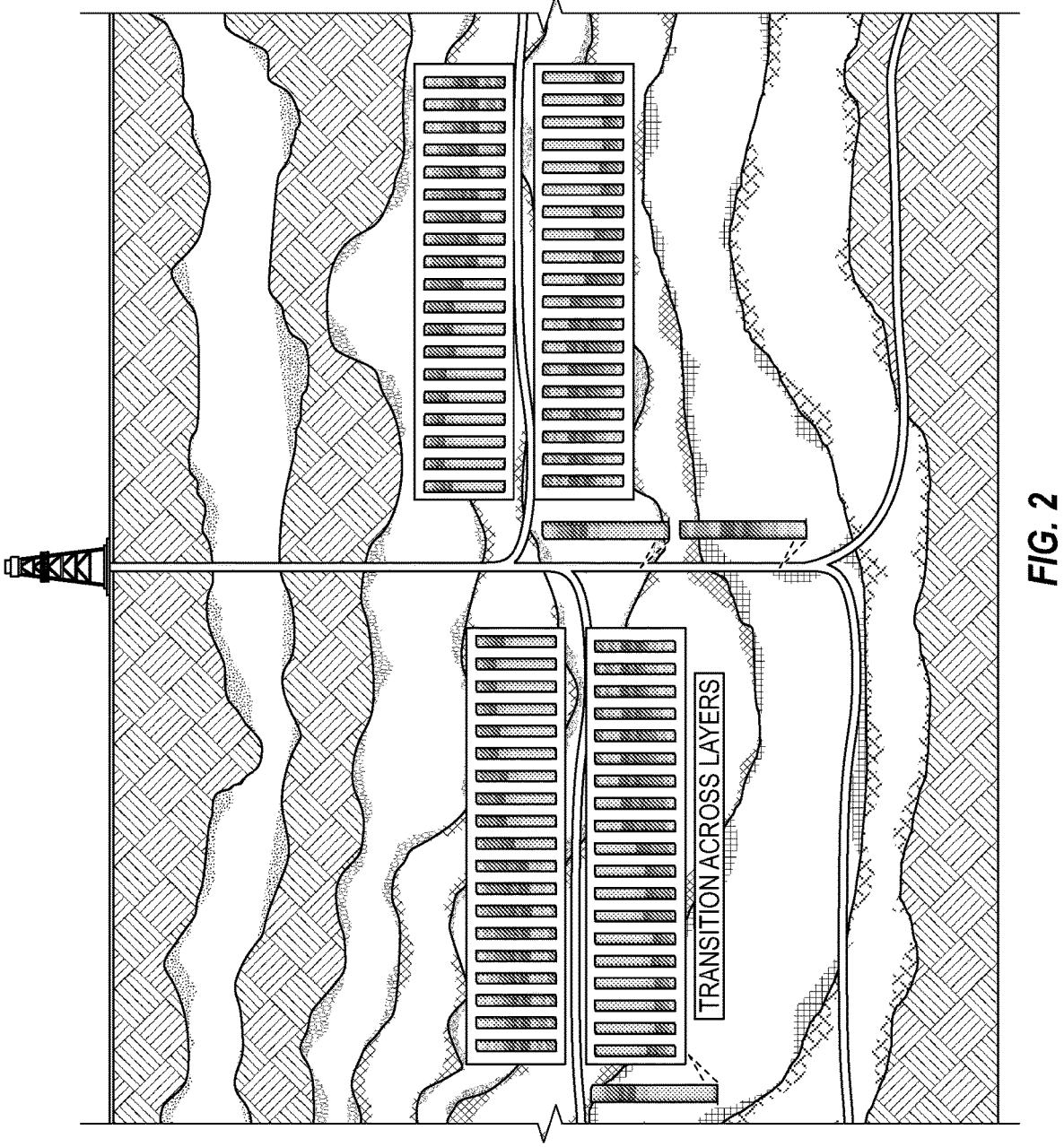
FIG. 2 is a diagram of the subset of dominant signatures sustained in the horizontal direction extracted from the vertical cuttings.

FIG. 2 is an example diagram of the subset of dominant signatures extracted from the vertical cuttings evolving in the horizontal direction. As shown in FIG. 2, some species that are highly abundant in the dominant may decline as you move along the horizontal direction, and other species that are found in low abundance near the vertical may increase in the horizontal direction.

BioGeo markers, BioGeo matrix, and/or BioGeo signatures may be generated based on the plurality of DNA profiles. A BioGeo marker for a location may represent the DNA of geological specimen at the location. A BioGeo marker may represent the DNA of the geological specimen at the location by defining, identifying, characterizing, and/or otherwise representing the identity/type of geological specimen found at the location (e.g., found in cuttings from the location), the amount (e.g., copy number, frequency, concentration) of the geological specimen found at the location. A BioGeo marker may represent both the actual amount of the geological specimen found at the location and the fractional amount of the geological specimen at the location. That is, a BioGeo marker may represent how much of different geological specimens were found at the location, and the relative abundance of the geological specimens at the location. A BioGeo marker may represent the combination of geological specimen present at a location and the frequency of the geological specimen at the location.

In some implementations, the BioGeo markers may be generated and/or filtered based on similarity of geological specimen across multiple locations. For example, for a region of interest (e.g., along a vertical part of a well, along a horizontal part of a well, along multiple/all parts of a well), samples may be recovered from multiple locations. Geological specimen information recovered from these samples that are not distinctive of any location may not be used in generation of the BioGeo markers. Alternatively, geological specimen information recovered from these samples that are not distinctive of any location may be removed (e.g., filtered out) from the BioGeo markers.

For example, for a region of interest, a particular geological specimen may be found in same abundance/concentration at all sample locations within the region of interest. Based on the particular geological specimen appearing in same concentration at all same locations within the region of interest, the particular geological specimen may not be included in the BioGeo markers for the region of interest (not included in original generation of the BioGeo markers; removed from the BioGeo markers).

A BioGeo signature for a location may represent unique DNA of geological specimens (e.g., unique type, unique amount/concentration, unique combination/ratio of different geological specimens) at the location. A BioGeo signature for a location may uniquely identify the location from other subsurface locations within the subsurface region.

A BioGeo signature for a location may be generated based on the BioGeo marker at the location and other BioGeo markers in other locations. While a BioGeo marker for a location may represent the species found at the location, a BioGeo signature for a location may represent both the species found at the location and the species not found at the location. The geological specimens identified by a BioGeo marker for a location may be compared with a list of potential geological specimens to determine which of the potential geological specimens are not identified by the BioGeo marker. Those potential geological specimens not identified by the BioGeo marker may be represented by the BioGeo signature for the location as not being present at the location. For example, based on a particular potential geological specimen not being identified by a BioGeo marker for a location, the BioGeo signature for the location may identify the particular potential geological specimen as missing from the location (e.g., amount/concentration of the particular potential geological specimen at the location being zero).

The list of potential geological specimens, to which the BioGeo markers are compared to generate the BioGeo signatures, may be determined (e.g., populated) based on the geological specimens identified as being present by the BioGeo markers in a region of interest. The region of interest that defines the list of potential geological specimens may be static or dynamic. For example, referring to FIG. 1, the region of interest to generate BioGeo signatures for locations along Horizontal #1 may include just the Horizontal #1, or combination of the Horizontal #1 with one or more other parts of the well. For example, the region of interest may include all horizontal and vertical parts of the well, and all geological specimens found throughout the well may be listed as potential geological specimens. As another example, the Horizontals #1 and #3 may be combined to form one region of interest while the Horizontals #2 and #4 may be combined to form another region of interest. The two regions of interest may have different list of potential geological specimens based on different sets of geological specimens being found along the different horizontal parts of the well.

In some implementations, the region of interest to define the list of potential geological specimens may be determined based on knowledge/predictions about fractures under the ground. For example, it may be known/predicted that fractures along Horizontals #1 and #3 may meet. Based on this knowledge/prediction, the Horizontals #1 and #3 may be combined to form one region of interest.

Aggregation of geological specimens found in a region of interest to define the list of potential geological specimens may enable specific identification of which specimens to look for when generating the BioGeo signatures. Rather than searching for all known specimens and identifying every specimen that is not found at a location, specific specimens (found in the region of interest) may be searched for and marked as being present or not present. Rather than searching for all known specimens and identifying every specimen that is not found at a location, BioGeo signatures may be generated by looking for specimen that is located at least once within the region of interest.

Aggregation of geological specimens found in a region of interest to define the list of potential geological specimens, and use of the list to add non-present specimens to the BioGeo signatures may enable more accurate/precise use of specimen information to identify source of material extracted from the ground. Generating the BioGeo signatures to identify non-present specimens may substantially improve signal-to-noise ratio and enable more accurate use of specimen information.

Figure 3:
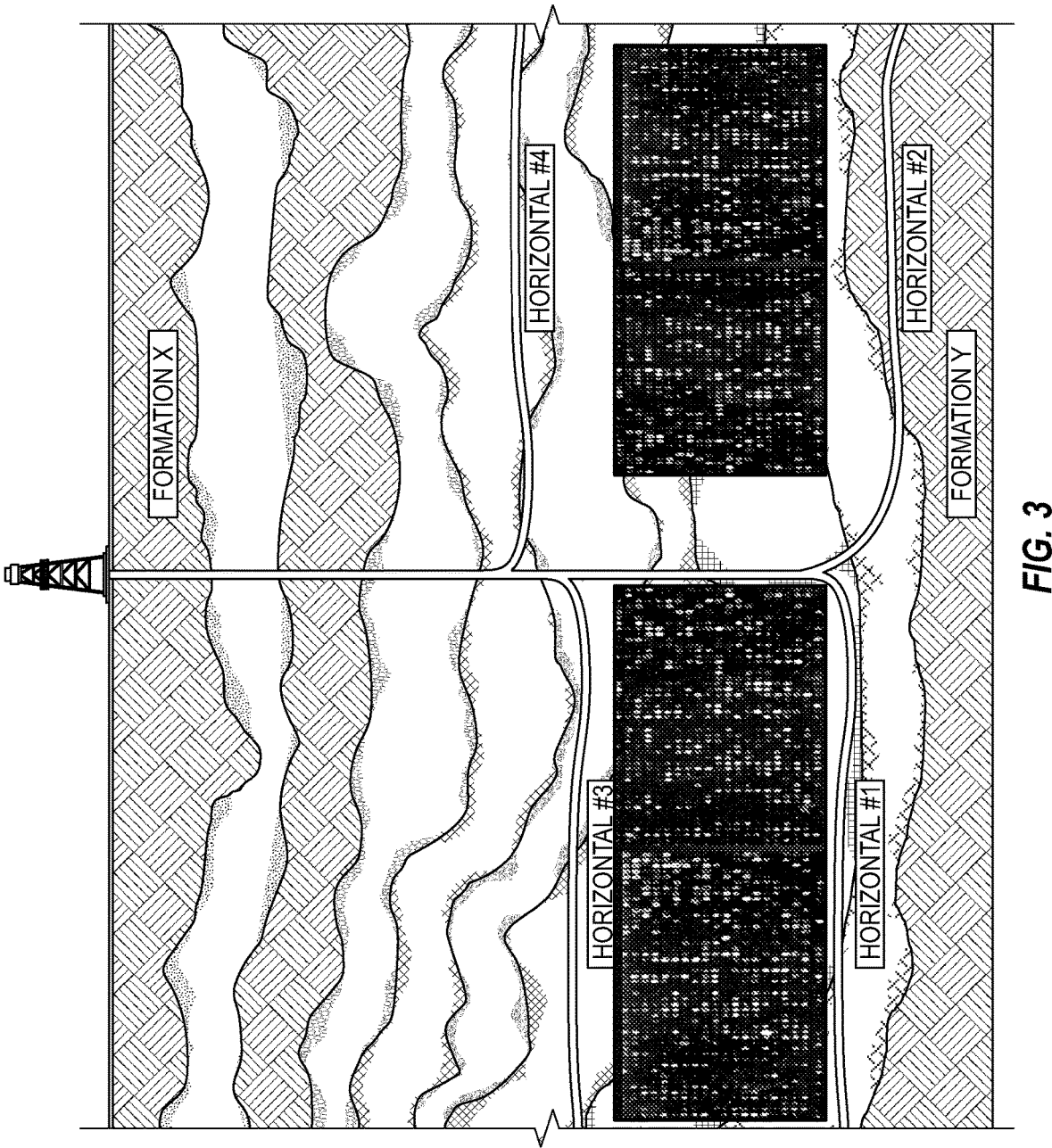
FIG. 3 is an illustration of a concept for generating a BioGeo Matrix as applied to geological formations at various depths, in accordance with this disclosure.

A BioGeo matrix may identify the BioGeo signatures for different subsurface locations. A BioGeo matrix may provide distribution and concentration of geological specimens at different subsurface locations within a subsurface region. BioGeo markers and/or BioGeo signatures generated from samples recovered from the well may provide data points (e.g., sparse data points) for the BioGeo matrix. Empty cells in the BioGeo matrix may be filled using the data points from the recovered samples. That is, based on geological specimens extracted from different locations in a subsurface region, likely distribution and concentration of the geological specimens at other locations in the subsurface region may be determined (e.g., ascertained, calculated, estimated, identified, predicted). In some implementations, a BioGeo matrix may be generated by predicting the distribution of differentially expressed species extracted from a sparse set of data points (e.g., cuttings) to the entire region of interest (e.g., basin) based on the dynamics of the signatures at different locations. Both species present and species absent may be taken into account in generation of the BioGeo matrix. An example BioGeo matrix is shown in FIG. 3, with different shadings of various cells indicating different combinations of present and absent species. In some implementations, the BioGeo matrix for a given region of interest (e.g., reservoir of interest) may be generated by extracting the minimum number of BioGeo markers that can explain a certain amount of (e.g., nearly 90%) of the variability observed in the original matrix.

The DNA profiles may be used to determine information about the subsurface region. The DNA profiles may be used to determine information about the wells in the subsurface region. Determination of information based on the DNA profile may include use of the DNA profile to determine the information. Determination of information based on the DNA profile may include use of BioGeo markers, BioGeo signatures, and/or BioGeo matrix (which are dependent on the DNA profile) to determine the information.

For example, spatial locations of geological specimens in a subsurface region may be determined based on the DNA profile. That is, spatial variability of geological specimens in a subsurface region (how geological specimens changes over different locations) may be determined based on the DNA profile. As another example, temporal changes in the geological specimens in a subsurface region may be determined based on the DNA profile. That is, temporal variability of geological specimens in a subsurface region (how geological specimens changes over time, such as based on hydrocarbon extraction and/or deposition of soil) may be determined based on the DNA profile.

Referring back to FIG. 8, At step 804, the controller determines fracture/drainage heights of the plurality of wells based on the plurality of DNA profiles. The determination may be based on a neural network, or other suitable machine learning network. A fracture/drainage height may refer to the length of a crack from a well (e.g., vertical growth of a fracture along a horizontal segment of a well). Fluid extracted from a location may carry geological specimens from the location. For example, BioGeo signatures may be extracted from product fluids for a duration of production cycle during hydraulic fracturing. The geological specimen present in the fluid may be matched to the geological specimen represented by the DNA profile. For example, distinctive traits (e.g., identity, concentration, combination) of geological specimens in the fluid extracted from the well may be matched to distinctive traits in the BioGeo signatures and/or the BioGeo matrix to identify the location(s) from which the fluid was extracted. Match may be made to a specific BioGeo signature/specific cell in the BioGeo matrix or to combination of BioGeo signatures/cells in the BioGeo matrix. The fracture/drainage height may be determined to be the distance between the identified location and the horizontal segment of the well.

Other information about the fracture/drainage may be determined based on the plurality of DNA profiles. For example, fracture/drainage lengths of the wells may be determined based on the plurality of DNA profiles. A fracture/drainage length may refer to a lateral position (e.g., lateral growth) of a fracture along a well.

At step 806, the controller determines a percent contribution from each of the wells of the plurality of wells based on the plurality of DNA profiles. The determination may be based on a neural network, or other suitable machine learning network or analytical techniques. A percent contribution may refer to how much of the extracted fluid came from different segments of a well. The source from which materials are extracted may be determined by matching the distinctive traits of the geological specimens in the extracted fluid to distinctive traits in the BioGeo signatures and/or the BioGeo matrix.

Figure 4:
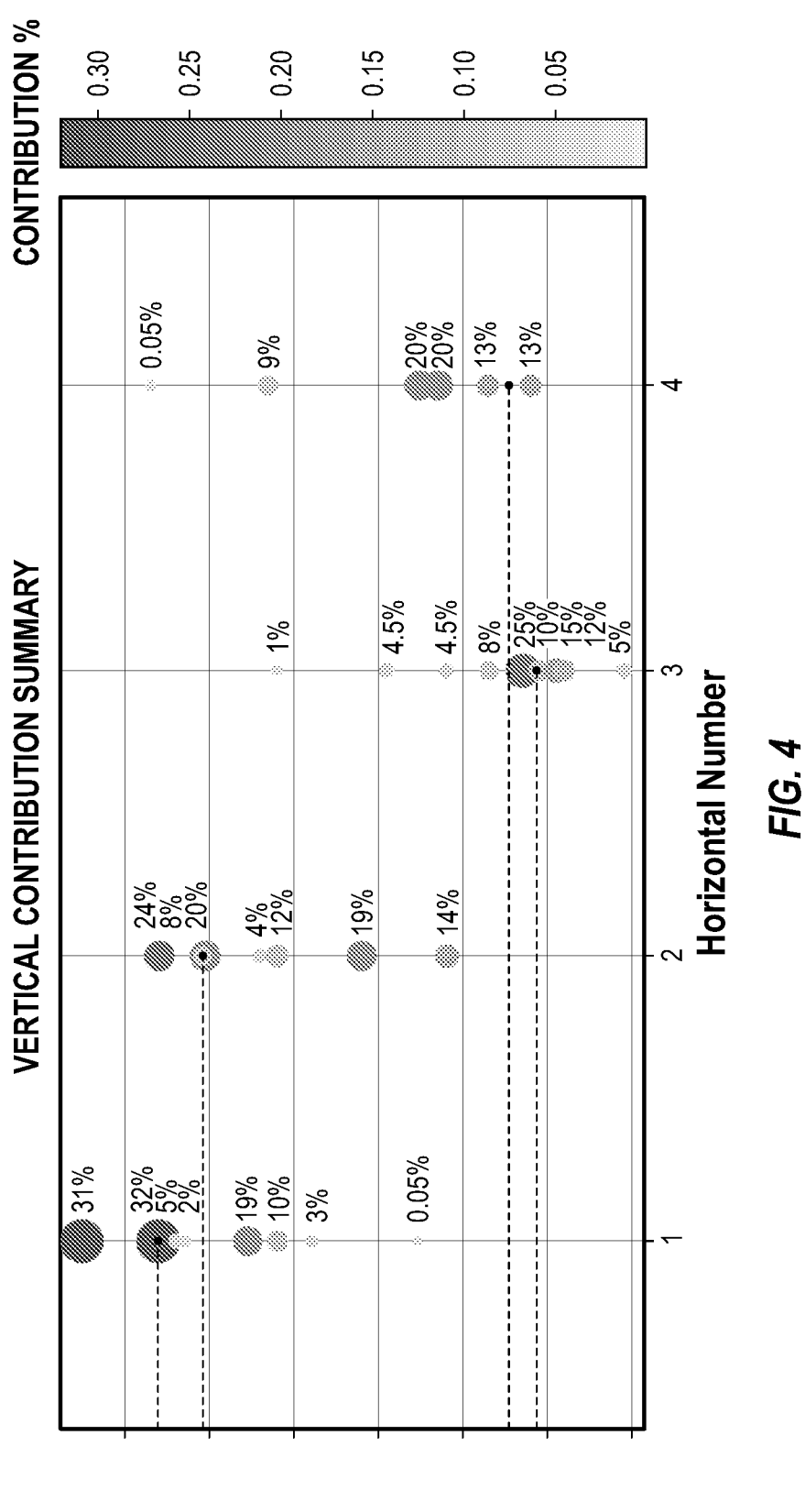
FIG. 4 is a graph illustrating the predicted percent contributions as related to fracture heights, in the vertical axis in accordance with this disclosure.
Figures 5A, 5B, 5C, 5D:
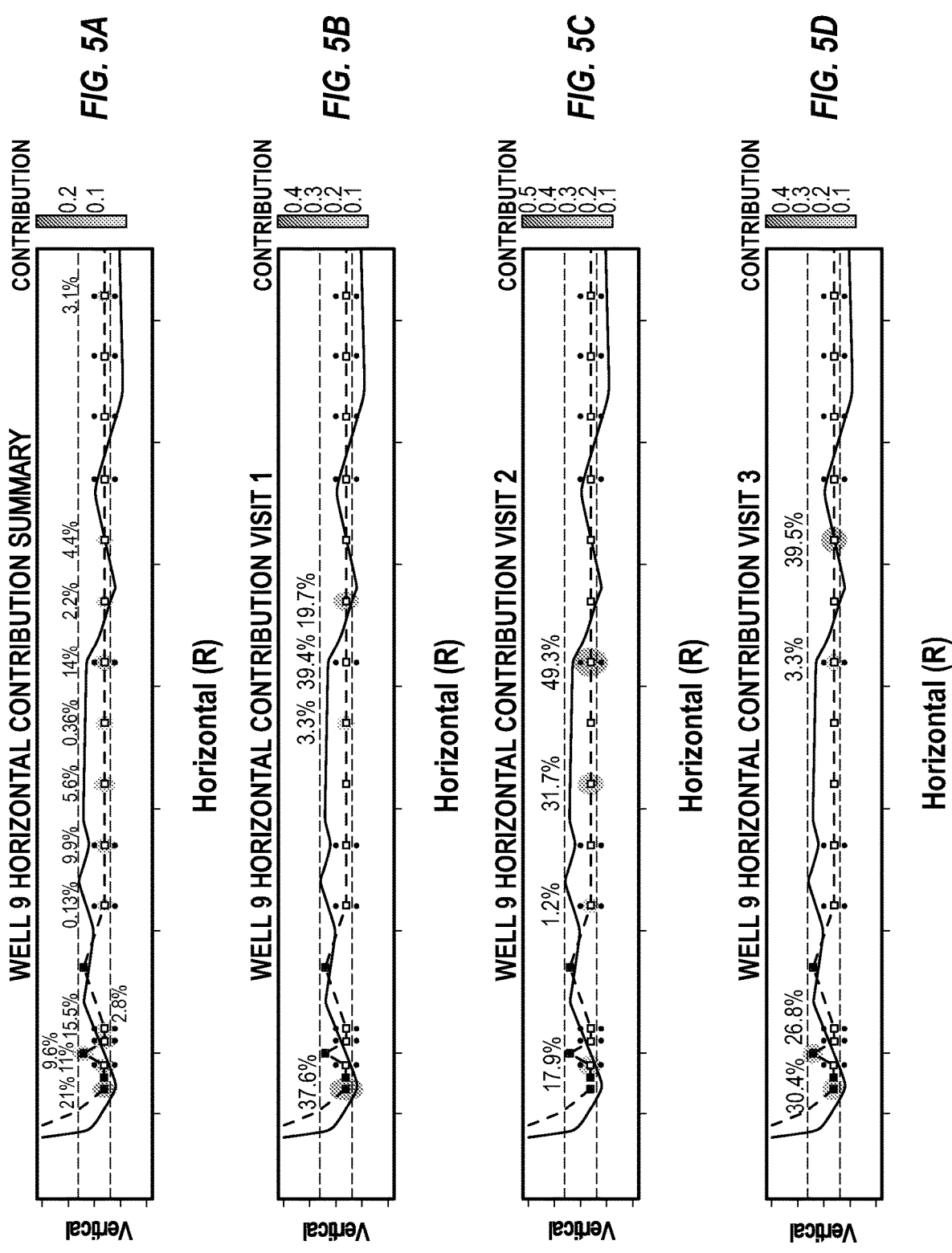
FIGS. 5A, 5B, 5C, and 5D are graphs illustrating the predicted percent contributions along the horizontal wells, monitored through the production cycle in accordance with this disclosure.

FIG. 4 shows an example vertical contribution of a well. A vertical contribution of a well may refer to how much of the extracted fluid came from different vertical locations along segments of the well. For example, the vertical contribution shown in FIG. 4 may indicate contribution of extracted fluid from the vertical locations along four different horizontals of a well. Dashed lines in FIG. 4 may indicate the depth at which the different horizontals are drilled. The vertical contribution of the well may be generated by extracting BioGeo signatures from the extracted fluids and mapping them on the BioGeo matrix. The relative amounts of species (e.g., DNA sequence copy number)

detected in the extracted fluid may be used to determine the percent contribution from different heights.

For example, referring to FIG. 4, 32% of the fluids from Horizontal #1 may be identified (using BioGeo signature) as coming from a particular depth, 31% of the fluids from this horizontal may be identified as coming from above this depth, and rest of the fluids from this horizontal may be identified as coming from multiple locations below this depth. Such identification of vertical contribution may provide insights on the height of fractures along the horizontals (e.g., shows the extent of fracturing, fracture height). In some implementations, the vertical contribution summary may be used to identify mixing between horizontals. For example, if a large percent of fluid for two horizontals are coming from similar vertical depth between the horizontal, this may indicate that the two horizontals that tapping into the same fluid source and/or that connection exist between fractures of the two horizontals.

Percent contribution of a well may change over time. For example, as fluids are extracted from a well, the fractures in the well may change (e.g., new opening created to a hydrocarbon source, an existing opening to a hydrocarbon source being closed), causing different recovery of fluid through the fractures. Changes in the recovery of fluid (e.g., changes in geological specimens recovered with fluid) may indicate changes in contribution of different segments of the well to extraction. For example, changes in the geological specimens recovered with fluid may be used to determine changes in percent contribution from fractures in the well (e.g., percent contribution from different fracture heights, percent contribution from fractures in different stages of the well (stage contribution)).

FIGS. 5A, 5B, 5C, and 5D show changes in contribution of a well over time, with visits being space apart by a duration of time. Changes in contribution of a well over time may be determined by incorporating data collected at defined intervals from production fluids throughout the production cycle. For instance, the most abundant species differentially expressed at the fracture heights calculated may be tracked along the horizontals.

FIGS. 5A, 5B, 5C, and 5D show that the contribution of different segments along the horizontal changes with time. Initially, during Visit 1, majority of the production may have come from two locations. During Visit 2, the contribution from the above depths may have dropped significantly (from 37.6% to 17.9%) while the contribution from around another depth may have increased to 31.7%. During Visit 3, the contribution may have shifted to have majority of the production come from different depths. Thus, the BioGeo signatures may be used to track dynamic changes in production profile of a well.

Referring back to FIG. 8, at step 808, the controller determines well connectivity for each of the wells of the plurality of wells. The determination may be based on a neural network, or other suitable machine learning network or analytical techniques. Well connectivity may refer to an extent to which multiple wells are connected. Two wells may be connected based on connection between fractures of the two wells. Two wells may be connected based on connecting to the same fluid source (e.g., two wells connected and drawing from the same reservoir). Connectivity of wells may be determined based on matching of geological specimens in fluid extracted from the wells. The extent of similarity between the geological specimens in fluid extracted from the wells may indicate the extent to which the wells are connected. For example, when two wells are connected, the extracted fluids from the two wells may include the same geological specimens. The geological specimens in fluid extracted from the wells may be used to determine which/when the wells are connected, and which/when the wells are disconnected.

The DNA profiles may be used to determine information about hydrocarbons in the subsurface region. Distinctive traits of geological specimens in the subregion region may correspond to presence of hydrocarbon in the subsurface region. For example, a particular combination of geological specimens may be present in locations in which hydrocarbons/particular amount of hydrocarbons are present. A map of hydrocarbon footprint may be generated based on the plurality of DNA profiles. A map of hydrocarbon footprint may refer to a map of a surface region that visually indicates areas/volumes in which hydrocarbons are (likely) present. In some implementations, a BioGeo matrix for the subsurface region (e.g., basin) may be decomposed to determine the optimal number of clusters that partition the subsurface region into discrete BioGeo clusters. The discrete BioGeo clusters may be used to generate a personalized map of geological subsurface zones of hydrocarbon potential.

For example, specific combinations of geological specimen may indicate (likely) presence/non-presence of hydrocarbon in a location, and the map (e.g., heat map) may visually indicate the locations in which hydrocarbons are or are not (likely) present. As another example, different traits of geological specimens may correspond to different amount of hydrocarbon in the subsurface region, and the map may visually indicate the (likely) quantity of hydrocarbon in different locations. The map of hydrocarbon footprint may be displayed on one or more graphical user interface. The map of hydrocarbon footprint may be displayed on one or more displays.

Certain embodiments of the present disclosure may include some, all, or none of the above advantages and/or one or more other advantages readily apparent to those skilled in the art from the figures, descriptions, and claims included herein. Moreover, while specific advantages have been enumerated above, the various embodiments of the present disclosure may include all, some, or none of the enumerated advantages and/or other advantages not specifically enumerated above.

Any of the herein described methods, programs, algorithms, or codes may be converted to, or expressed in, a programming language or computer program. The terms "programming language" and "computer program," as used herein, each include any language used to specify instructions to a computer, and include (but is not limited to) the following languages and their derivatives: Assembler, Basic, Batch files, BCPL, C, C+, C++, Delphi, Fortran, Java, JavaScript, machine code, operating system command languages, Pascal, Perl, PL1, scripting languages, Visual Basic, metalanguages which themselves specify programs, and all first, second, third, fourth, fifth, or further generation computer languages. Also included are database and other data schemas, and any other meta-languages. No distinction is made between languages which are interpreted, compiled, or use both compiled and interpreted approaches. No distinction is made between compiled and source versions of a program. Thus, reference to a program, where the programming language could exist in more than one state (such as source, compiled, object, or linked) is a reference to any and all such states. Reference to a program may encompass the actual instructions and/or the intent of those instructions.

It should be understood the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached figures are presented only to demonstrate certain examples of the disclosure. Other elements, steps, methods, and techniques that are different from those described above and/or in the appended claims are also intended to be within the scope of this disclosure.

What is claimed is:

1. A method for analytic mapping of metagenomic and hydrocarbon footprints of geologic subzones, the method comprising:

generating a plurality of DNA profiles for individual ones of a plurality of wells through the geologic subzones based on a set of distinct geological specimens from each well of the plurality of wells, wherein a given DNA profile of a given well represents DNA species from the geological specimens as a function of position within the given well; and generating BioGeo markers, BioGeo signatures and a BioGeo matrix based on the plurality of DNA profiles, wherein generating the BioGeo markers from the DNA profiles includes identifying a first DNA species present in substantially similar concentrations across the set of distinct geological specimens and excluding the first DNA species from the BioGeo markers as noise.

2. The method of claim 1, further comprising determining fracture/drainage height from each of the wells of the plurality of wells based on the plurality of DNA profiles.

3. The method of claim 1, further comprising determining a percent contribution from each of the wells of the plurality of wells based on the plurality of DNA profiles.

4. The method of claim 1, further comprising determining a percent contribution from fractures in each stage of the wells of the plurality of wells based on the plurality of DNA profiles.

5. The method of claim 1, further comprising determining stage contribution along a horizontal well of the plurality of wells based on the plurality of DNA profiles.

6. The method of claim 1, further comprising determining well connectivity for each of the wells of the plurality of wells.

7. The method of claim 1, wherein the distinct geological specimens include at least one of cuttings, drilling mud, and produced fluids.

8. The method of claim 1, further comprising generating a map of the hydrocarbon footprint based on the plurality of DNA profiles and displaying the map of one of the hydrocarbon footprints on a graphical user interface.

9. The method of claim 1, further comprising generating a plurality of BioGeo clusters by performing unsupervised hierarchical clustering of the BioGeo signatures, wherein the plurality of BioGeo clusters divide the geologic subzones based on contributions of the BioGeo signatures individually.

10. The method of claim 1, further comprising determining fracture lengths of the plurality of wells based on the plurality of DNA profiles.

11. A system for analytic mapping of metagenomic and hydrocarbon footprints of geologic subzones, the system comprising:

at least one processor;

a graphical user interface; and a memory, including instructions, which when executed by the at least one processor, cause the system to:

generate a plurality of DNA profiles for individual ones of a plurality of wells through the geologic subzones based on a set of distinct geological specimens from each well of the plurality of wells, wherein a given DNA profile of a given well represents DNA species from the geological specimen as a function of position within the given well; and generate BioGeo markers, BioGeo signatures and a BioGeo matrix based on the plurality of DNA profiles, wherein generating the BioGeo markers from the DNA profiles includes identifying a first DNA species present in substantially similar concentrations across the set of distinct geological specimens and excluding the first DNA species from the BioGeo markers as noise.

12. The system of claim 11, wherein the instructions, when executed by the at least one processor, further cause the system to determine fracture/drainage height from each of the wells of the plurality of wells based on the plurality of DNA profiles.

13. The system of claim 11, wherein the instructions, when executed by the at least one processor, further cause the system to determine a percent contribution from each of the wells of the plurality of wells based on the plurality of DNA profiles.

14. The system of claim 11, wherein the instructions, when executed by the at least one processor, further cause the system to determine a percent contribution from fractures in each stage of the wells of the plurality of wells based on the plurality of DNA profiles.

15. The system of claim 11, wherein the instructions, when executed by the at least one processor, further cause the system to determine stage contribution along a horizontal well of the plurality of wells based on the plurality of DNA profiles.

16. The system of claim 11, wherein the instructions, when executed by the at least one processor, further cause the system to determine well connectivity for each of the wells of the plurality of wells.

17. The system of claim 11, wherein the distinct geological specimens include at least one of cuttings, drilling mud, and produced fluids.

18. The system of claim 11, wherein the instructions, when executed by the at least one processor, further cause the system to generate a map of one of the hydrocarbon footprints based on the plurality of DNA profiles and display the map of the hydrocarbon footprint on the graphical user interface.

19. The system of claim 11, wherein the instructions, when executed by the at least one processor, further cause the system to generate a plurality of BioGeo clusters by performing unsupervised hierarchical clustering of the BioGeo signatures, wherein the plurality of BioGeo clusters divide the geologic subzones based on contributions of the BioGeo signatures individually.

20. The system of claim 11, wherein the instructions, when executed by the at least one processor, further cause the system to determine fracture lengths of the plurality of wells based on the plurality of DNA profiles.

* * * * *